(12) United States Patent
Maguire et al.

(10) Patent No.: US 10,912,885 B2
(45) Date of Patent: Feb. 9, 2021

(54) DEVICE AND METHOD FOR INFUSING AND ASPIRATING FLUID

(71) Applicant: AngioDynamics, Inc., Latham, NY (US)

(72) Inventors: Shannon Maguire, Newtonville, MA (US); Anthony Hien, Stoneham, MA (US)

(73) Assignee: AngioDynamics, Inc., Latham, NY (US)

( * ) Notice: Subject to any disclaimer, the term of this patent is extended or adjusted under 35 U.S.C. 154(b) by 115 days.

(21) Appl. No.: 16/053,690

(22) Filed: Aug. 2, 2018

(65) Prior Publication Data

US 2019/0060564 A1  Feb. 28, 2019

Related U.S. Application Data

(60) Provisional application No. 62/540,276, filed on Aug. 2, 2017.

(51) Int. Cl.
*A61M 39/02* (2006.01)
*A61M 5/158* (2006.01)
*A61M 5/14* (2006.01)
*A61M 39/00* (2006.01)

(52) U.S. Cl.
CPC ............ *A61M 5/158* (2013.01); *A61M 39/02* (2013.01); *A61M 39/0208* (2013.01); *A61M 2005/1403* (2013.01); *A61M 2039/0009* (2013.01); *A61M 2039/0205* (2013.01); *A61M 2206/14* (2013.01); *A61M 2206/16* (2013.01); *A61M 2206/20* (2013.01); *A61M 2206/22* (2013.01)

(58) Field of Classification Search
CPC .......... A61M 2005/1403; A61M 5/141; A61M 5/16804; A61M 2005/1587; A61M 2005/14252; A61M 2005/14284; A61M 2039/0009; A61M 2206/16; A61M 5/158
See application file for complete search history.

(56) References Cited

U.S. PATENT DOCUMENTS 3,244,109 A * 4/1966 Barske ................ F04D 29/2255
                                                    415/206
10,220,137 B2 * 3/2019 Sonderegger ......... A61M 5/162

* cited by examiner

*Primary Examiner* — Deanna K Hall
(74) *Attorney, Agent, or Firm* — Peter Flora

(57) ABSTRACT

The instant invention discloses a low-profile infusion set for the infusion and aspiration of fluid. The infusion set comprises an infusion tubing, an extension tube, a housing, a needle, and a needle holder. The extension tube and needle are connected to the housing, creating improved fluid pressure rates and flow rates.

18 Claims, 11 Drawing Sheets

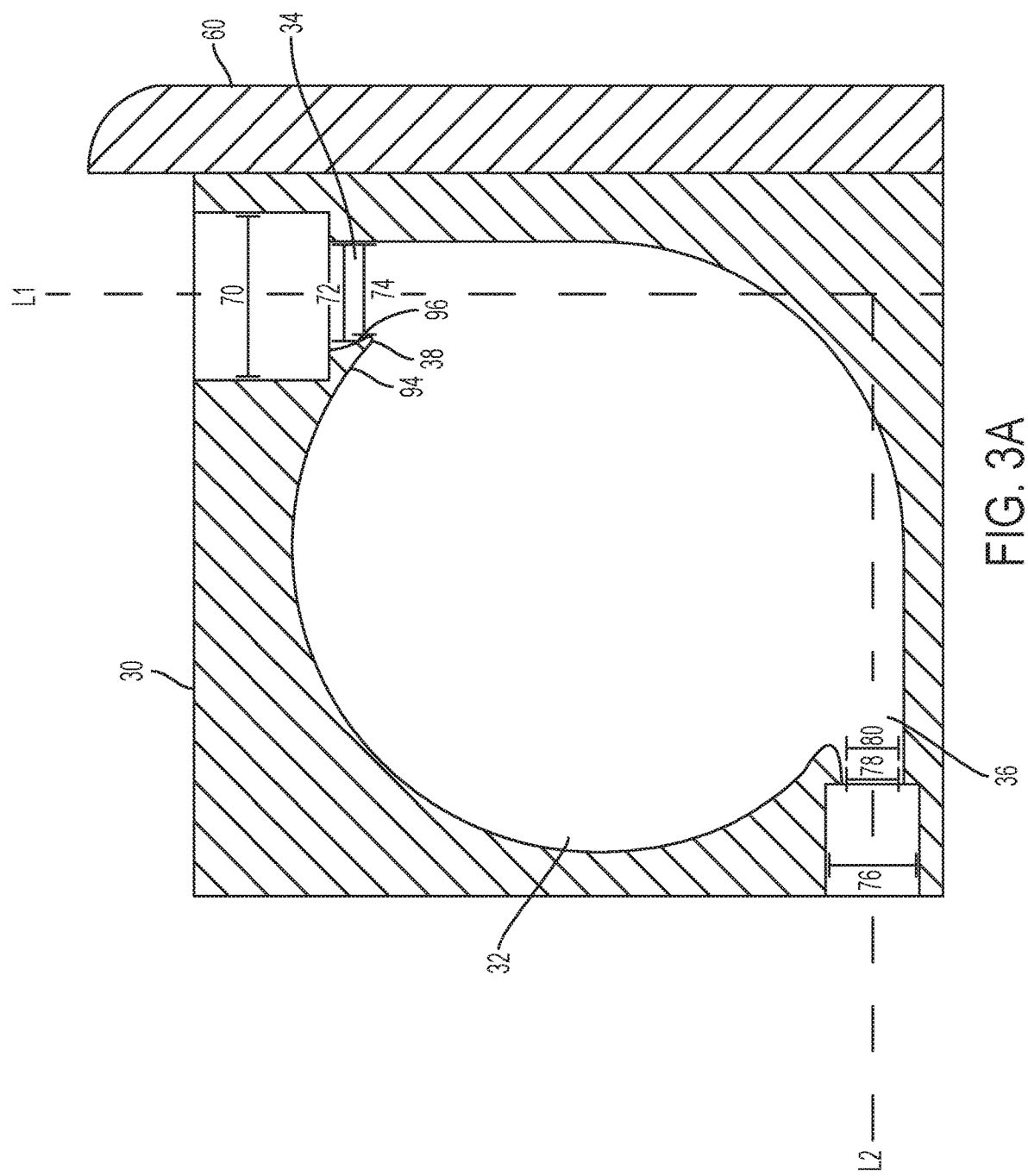

US 10,912,885 B2

DEVICE AND METHOD FOR INFUSING AND ASPIRATING FLUID

CROSS-REFERENCE TO RELATED APPLICATIONS

This application claims priority to and the benefit of U.S. Provisional Application 62/540,276, filed Aug. 2, 2017 and is hereby incorporated by reference.

BACKGROUND

The use of infusion sets to deliver and aspirate fluid to a patient through an implanted vascular access port is common in today's medical profession. The vascular access port is implanted beneath the skin of the patient and is accessed by the infusion set. This is accomplished by inserting a needle of the infusion set through a penetrable septum. The needle used to insert through the penetrable septum is preferably a non-coring needle. Infusion sets should be as low-profile as possible to minimize displacement during aspiration and infusion procedures. To address this need, needles in prior art infusion sets have been designed with a 90-degree bend. The 90-degree bend reduces the overall height of the infusion set, but also results in a lower fluid flow rate and more turbulent flow, which in turn causing an increase in pressure build up within the needle and decreased fluid pressure rate through the infusion set. There is a need in the art for an infusion set which has an overall low profile while minimizing fluid flow disruption.

FIELD OF THE INVENTION

The present invention generally relates to infusion devices. In particular, the invention is related to infusion needle devices and associated methods used to gain access to an implanted vascular access port for infusion and aspiration of fluids to a patient.

SUMMARY OF THE DISCLOSURE

The instant application discloses a device comprising a needle comprising a needle proximal end, and a needle distal end, an extension tube comprising an extension tube proximal end and an extension tube distal end, and a housing comprising a reservoir having a cylindrical shape, a first channel in fluid communication with the extension tube distal end, and a second channel in fluid communication with the needle proximal end.

Additionally, the first channel and second channel are located along a tangent to the reservoir. The housing further comprises a protrusion extending toward a first channel longitudinal axis, the protrusion comprising a first protrusion segment formed from a section of a wall of the reservoir and a second protrusion segment formed from a section of a wall of the first channel. The cylindrical shape of the reservoir is configured to provide a circumferential fluid flow. In alternate embodiments, the reservoir of the housing can also be toroidal or spherical in shape.

The instant application also discloses a method comprising the steps of accessing a site with an infusion set, the infusion set comprising a needle comprising a needle proximal end, and a needle distal end, an extension tube comprising an extension tube proximal end and an extension tube distal end, and a housing comprising a reservoir having a cylindrical shape, a first channel in fluid communication with the extension tube distal end, and a second channel in fluid communication with the needle proximal end, and flowing a fluid through the infusion set. The housing further comprises a protrusion configured to direct the fluid toward a wall of the reservoir in a direction away from a first channel longitudinal axis

BRIEF DESCRIPTION OF THE FIGURES

FIG. 3A is a cross section of the housing taken along line B-B in FIG. 2 in one embodiment.

DETAILED DESCRIPTION OF THE FIGURES

Laminar flow is a flow of fluid in which fluid travels smoothly and the velocity, fluid pressure, and other flow properties remain substantially constant within the fluid. Turbulent flow is a flow of fluid in which fluid undergoes irregular fluctuations and the velocity, fluid pressure, and other flow properties are continuously undergoing changes in both magnitude and direction. Circumferential flow is descriptive of the direction that a fluid is flowing in, namely, that the fluid flows around the circumference of the container it is within.

Figure 1:
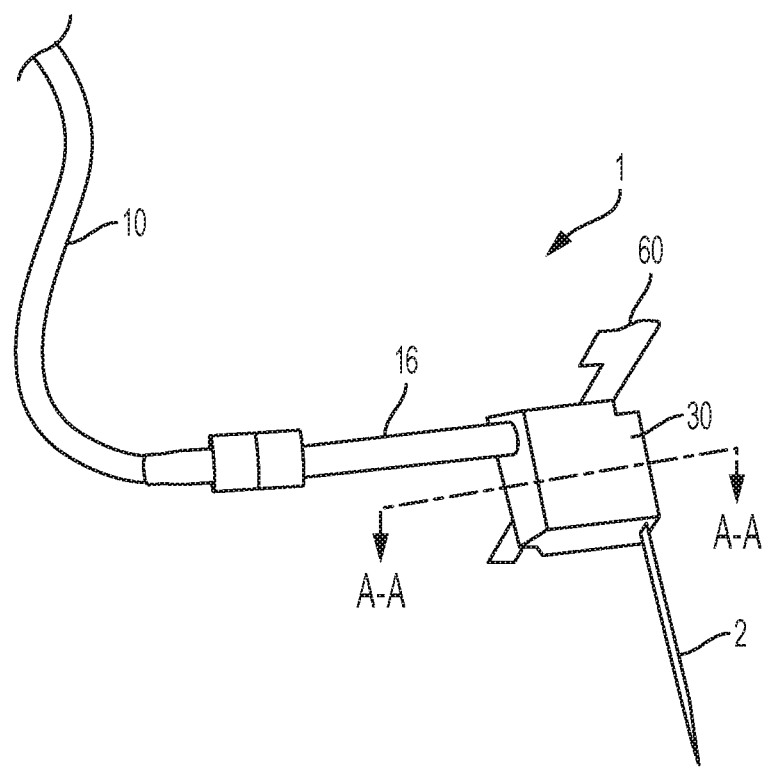
FIG. 1 is an isometric view of an embodiment of the infusion set of the current invention.
Figure 2:
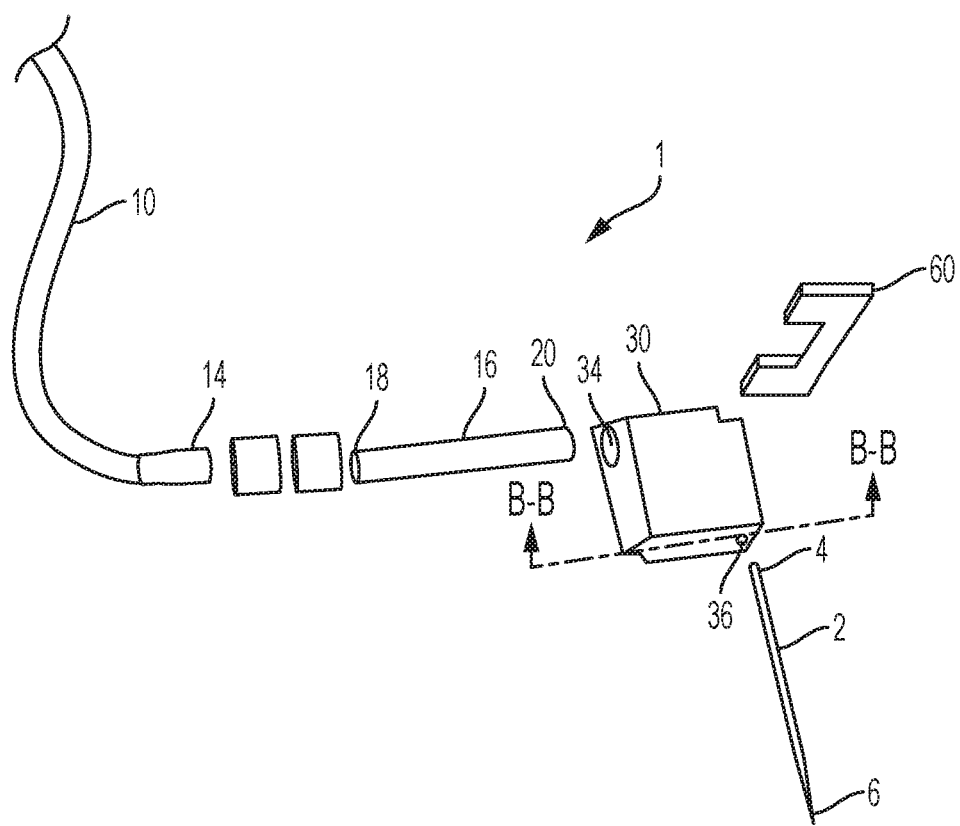
FIG. 2 is an exploded isometric view of an embodiment of the infusion set of the current invention.

Referring now to FIGS. 1-2, one embodiment of the infusion set 1 is shown. The term infusion set 1 is herein defined as not only for the use of the infusion of fluid but may also be used for the aspiration of fluid. The infusion set 1 may be comprised of a needle 2, infusion tubing 10, extension tube 16, a housing 30, and a needle holder 60. The housing 30 further comprises a first channel 34 and a second channel 36. The infusion tubing proximal end (not shown) may be first connected to a fluid source (not shown) or medical device for infusion or aspiration (not shown). The size of the housing 30 is intended to be compact for a low-profile design. The size of the housing 30 depicted in FIGS. 1-2 are for illustrative purposes only. The infusion tubing distal end 14 may be fluidly connected to the extension tube proximal end 18 by a luer attachment. The extension tube distal end 20 is connected to the first channel 34 of the housing 30. The proximal end 4 of the needle 2 is connected to the second channel 36 of the housing 30. The needle holder 60 is connected to the housing 30, and may include, but is not limited to, a winged needle holder as described in U.S. Pat. No. 6,676,633, filed Oct. 24, 2002 and is incorporated by reference. The infusion set 1 of the current invention may also comprise a safety feature capable of retracting and sheathing the needle, protecting the user from accidental injuries such as a needle stick. The safety feature is described in U.S. Pat. No. 6,676,633, filed Oct. 24, 2002 and is incorporated by reference.

The infusion set 1 has a decreased profile compared to prior art infusion systems having a linear fluid path. The decreased profile provides many benefits to the infusion set 1. A problem in the art with previously known infusion sets that have a higher profile is a lessened stability of the needle, as the center of gravity of the infusion set is spaced further from an implanted vascular access port or patient. The higher center of gravity makes the prior art infusion set more sensitive to equipment vibration, shifts in weight from the infusion tubing, or other disruptions. These disruptions may result in the prior art needle of the infusion set becoming dislodged, possibly damaging the septum of the implanted vascular access port, and/or causing discomfort to the patient. Additionally, it is more cumbersome to stabilize a prior art infusion set with a higher profile, as the user needs to use additional stabilization materials between the patient's skin surface and the needle housing of the prior art infusion set. The materials used to stabilize the infusion set include, but are not limited to gauze. The infusion system 1 of this application addresses these problems in the art by providing a low profile system of an extension tube 16, housing 30, and needle 2.

The infusion tubing 10 of the device comprises an infusion tubing proximal end (not shown) and an infusion tubing distal end 14. During an infusion procedure, the infusion tubing 10 can be fluidly connected to a fluid source or medical equipment for dialysis, apheresis, and power injection of fluid in order to assist in flowing fluid from the fluid source to the infusion set 1. During an aspiration procedure, such as dialysis or apheresis, the infusion tubing can also connect to a number of sources, including but not limited to medical equipment used to treat blood removed from a patient as known in the art.

The needle 2 comprises a needle proximal end 4, a needle distal end 6, and a needle longitudinal axis (not shown). The needle 2 is constructed such that the needle proximal end 4 is parallel to the needle longitudinal axis and the needle distal end 6 extends away from the needle longitudinal axis at a selected angle. The benefit of the needle distal end 6 extending away from the needle longitudinal axis at a selected angle is that the needle 2 will not core the septum of an implanted vascular access port. The needle 2 may be connected to the housing 30 at the second channel 36 by various means, including, but not limited to overmolding, adhesive, pressure fit, or friction fit.

The extension tube 16 may have a luer connection at the extension tube proximal end 18 in order to fluidly connect to the infusion tubing distal end 14. The extension tube distal end 20 may be connected to the housing 30 at the first channel 34 by various means, including, but not limited to overmolding, adhesive, pressure fit, or friction fit.

Prior art infusion sets typically include a bent needle having a 90 degree bend along the fluid path, for example a portion of the needle may be bent 90 degrees or a straight needle many connect to a perpendicular housing fluid channel creating a 90 degree angle. Turbulent fluid flow occurs in prior art infusion sets with a bent needle and can cause multiple performance issues, including, but not limited to decreased fluid pressure and decreased fluid flow rate. The decreased fluid pressure and flow rate limits the speed at which fluid can be flowed through the prior art infusion set having a bent fluid path, which can make procedures last longer than necessary.

One of the shortcomings of a prior art infusion set with a 90-degree bend in the fluid path is that it causes turbulent fluid flow during injection and hemolysis during procedures that include the aspiration and/or infusion of blood including, but not limited to during an apheresis procedure. Apheresis is a procedure used to remove unhealthy blood from a patient and pass it through a system, which will separate and/or collect a constituent of the blood to return to the patient for recirculation through the body. Hemolysis of blood is defined as the damaging or rupture of red blood cells. Hemolysis is common in apheresis procedures due to the turbulent flow that occurs in bent-needle prior art infusion sets when the blood flows along the wall of the needle at the bend, shearing and damaging the red blood cells in the blood being infused or aspirated. Alternatively, to avoid hemolysis straight needle sets may be used during an apheresis procedure, however these are not low profile in design. The infusion set 1 described herein provides the benefit of a low profile infusion set that minimizes hemolysis by eliminating the 90 degree bend in the fluid path.

Another shortcoming caused by the 90-degree bend in the fluid path of prior art infusion sets is that blood or other fluids can pool and build up at the bend, causing buildup that will further decrease the fluid pressure and flow rate of the fluid. The infusion set 1 of the current invention solves this problem by introducing a housing 30 with a reservoir 32 between the extension tube 16 and the needle, removing the need for a 90-degree bend in the fluid path.

An advantage of the extension tube 16 and needle 2 being connected to the reservoir 32 is that it allows for less fluid pressure buildup, given that the extension tube 16 does not need to connect directly to the needle 2. In prior art infusion sets where the needle is connected directly to the infusion tubing there is an abrupt change in diameter from a larger diameter to a smaller diameter causing fluid pressure buildup, thereby resulting in lower pressure rates and lower flow rates. Conversely, the infusion set 1 described herein includes a housing 30 with a reservoir 32 between the extension tube 16 and the needle 2, allowing for the fluid to be delivered at a higher pressure rate and a higher flow rate, as the needle 2 does not need to be directly connected to the extension tube 16 or infusion tubing 10, thereby making procedures quicker and more efficient.

Laminar flow into and out of the reservoir 32 is beneficial, as it allows for fluid to be delivered into the reservoir 32 at a higher pressure and flow rate. Increased laminar flow into the reservoir 32 of the instant invention will allow for a more circumferential flow within the reservoir 32. The circumferential flow within the reservoir 32 can lessen the amount of clogs and clots in the reservoir 32, as the fluid can flow at a higher velocity and rate due to an increased laminar flow compared to a standard infusion needle having a bend or an infusion set having a bend or angle within the fluid path.

Figure 3B:
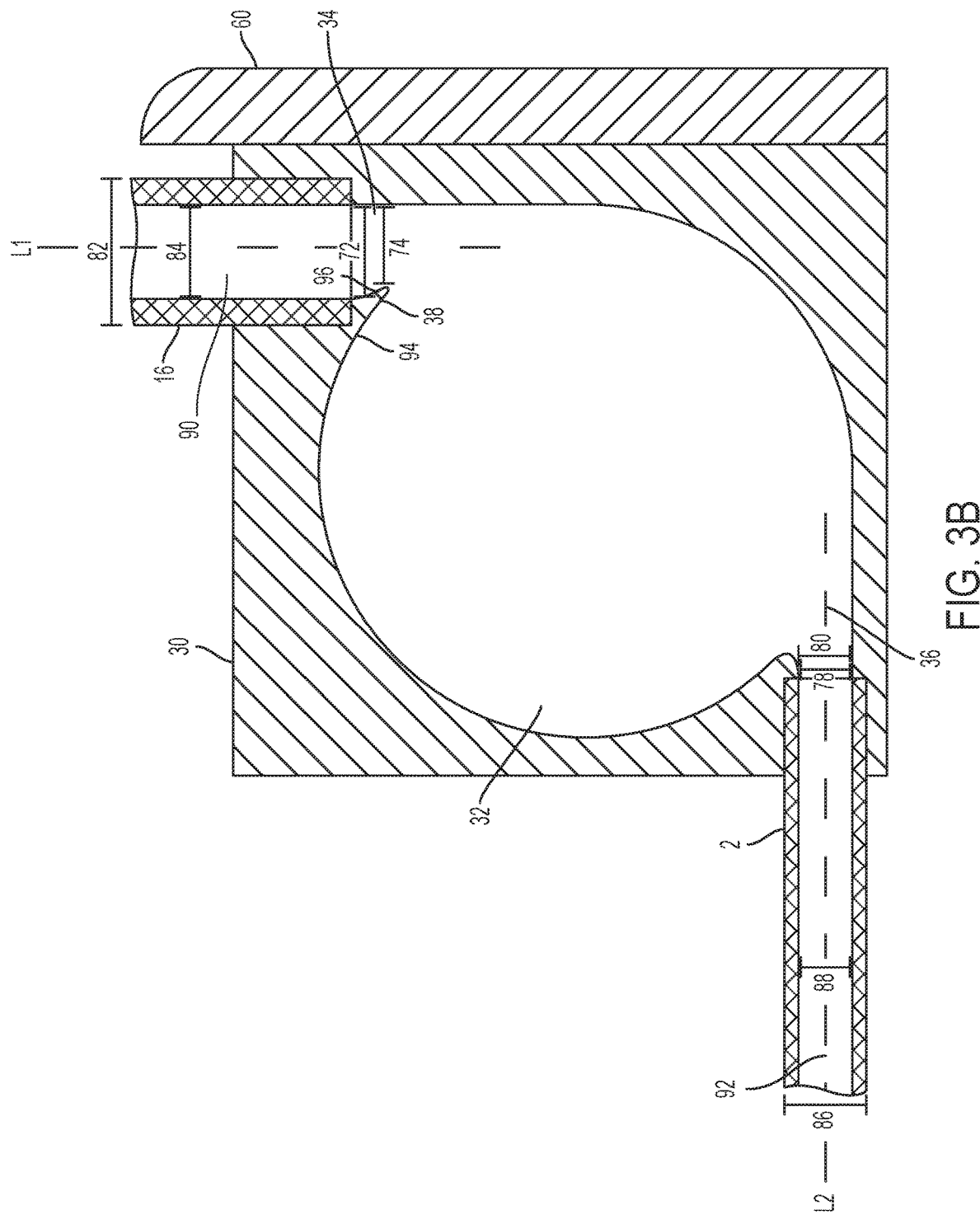
FIG. 3B is a cross section of the housing taken along line B-B in FIG. 2 illustrating the needle and extension tubing connections.
Figure 3C:
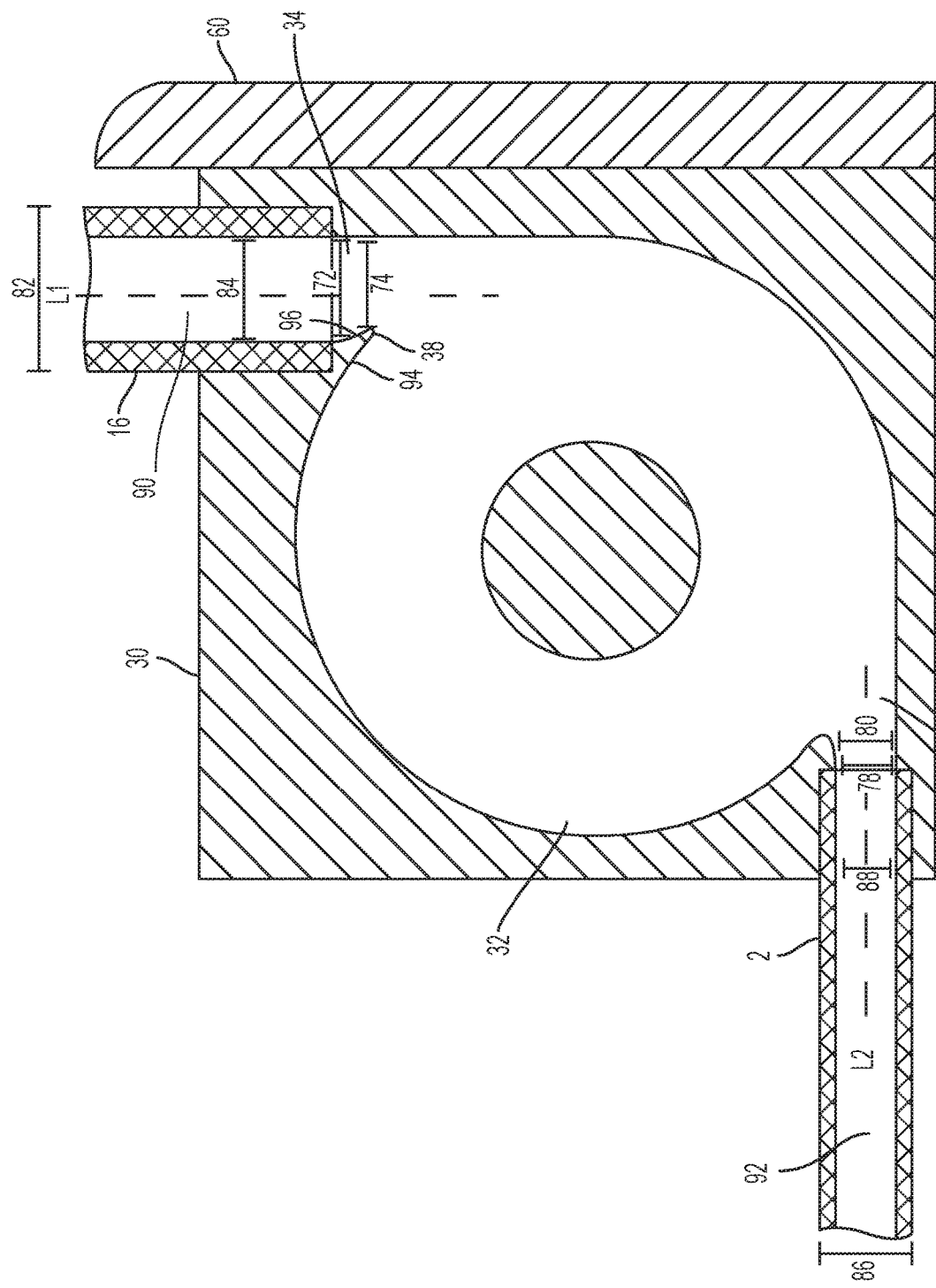
FIG. 3C is a cross section of the housing taken along line B-B in FIG. 2 in another embodiment.
Figure 5:
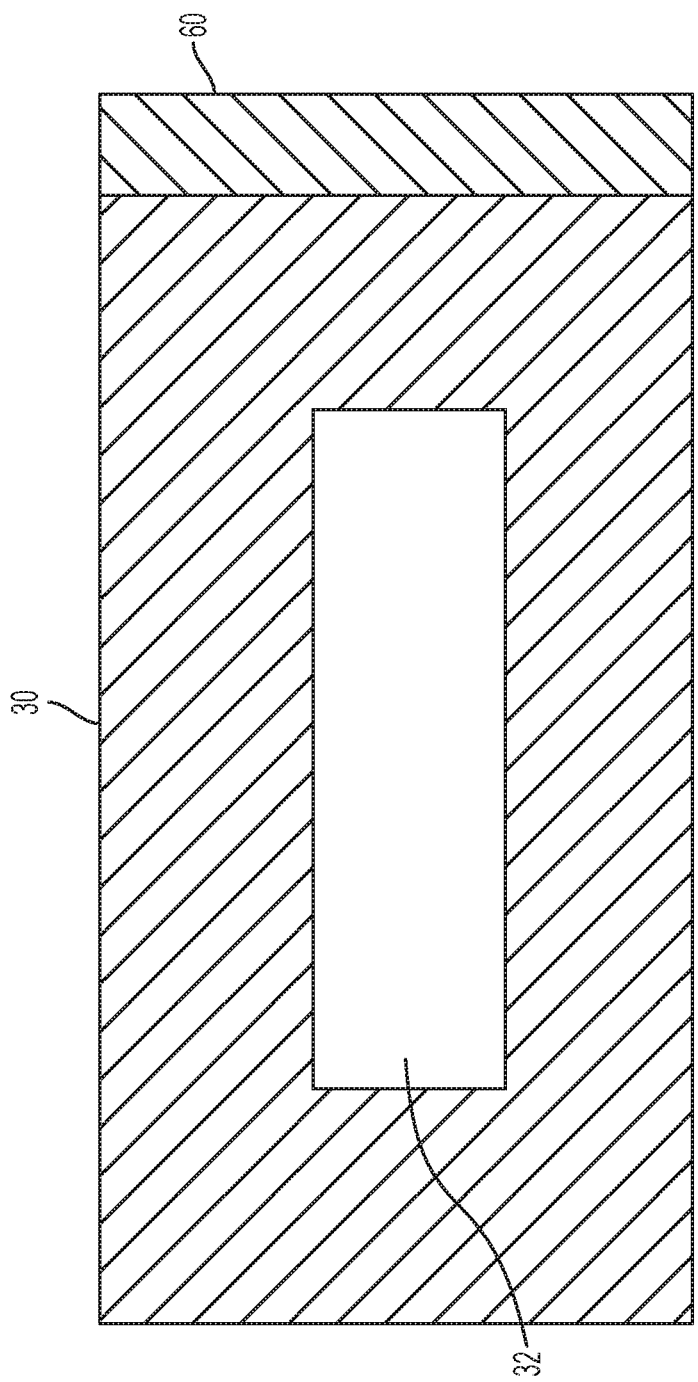
FIG. 5 is a cross section of the housing along the line A-A in FIG. 1 illustrating the reservoir in the embodiment shown in FIG. 3A.
Figure 6:
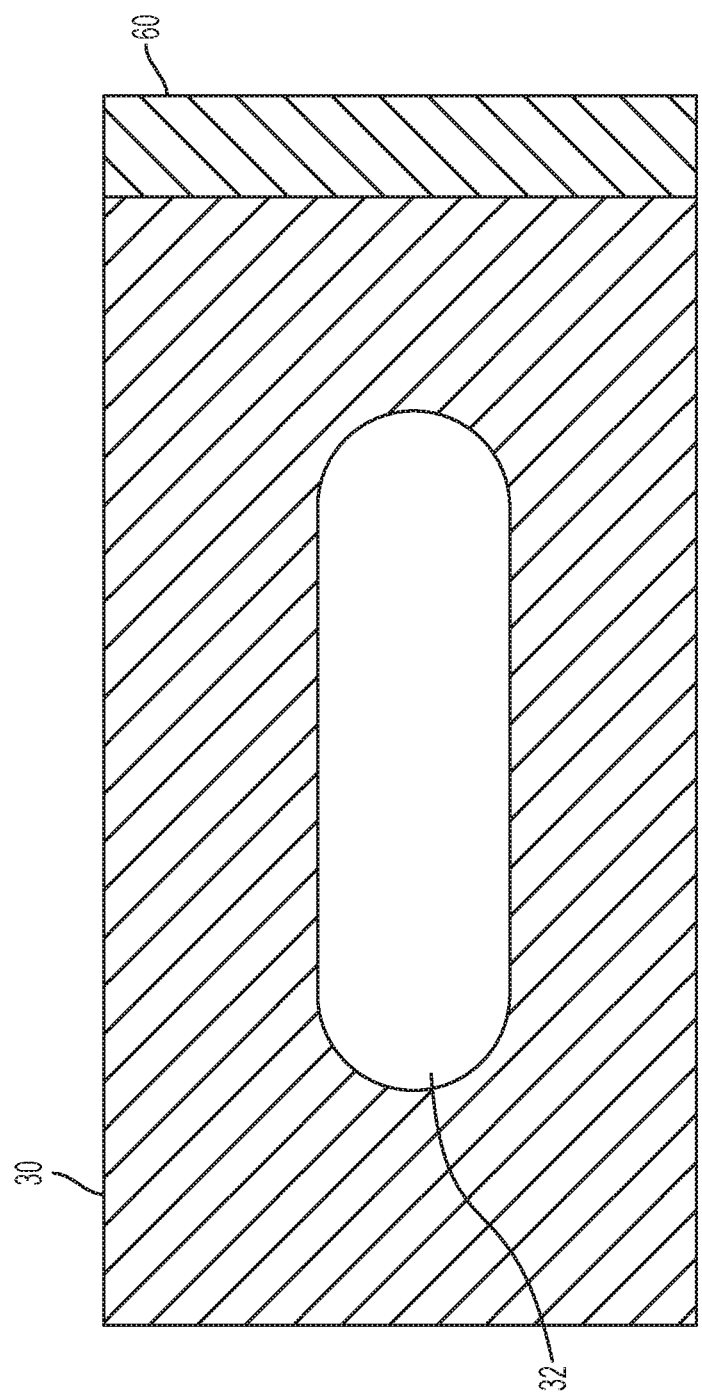
FIG. 6 is a cross section of the housing along the line A-A in FIG. 1 illustrating the reservoir in an alternative embodiment.

Referring now to FIGS. 3A-3C, a cross-section of the housing 30 taken along line B-B of FIG. 2 is shown. The housing 30 comprises a reservoir 32, a first channel 34, a second channel 36, a protrusion 38, and a needle holder 60. The housing 30 can be constructed in multiple ways. One way may be to have the housing 30 consist of two halves and then form a single piece of material including, but not limited to plastic or other method known in the art, using a number of methods, including, but not limited to ultrasonic welding. The housing 30 could also be made from a single piece of material including, but not limited to plastic or other method known in the art created through an injection molding or other processes known in the art. In one embodiment, as shown in FIGS. 3A-3B the reservoir 32 of the housing 30 may have a cylindrical shape defined as a geometric figure with straight parallel sides and a circular cross section. FIG. 5 represents a cross section of the housing 30 taking along lines A-A of FIG. 1, depicting the cylindrical shape of the reservoir 32 with straight and parallel sides. FIG. 6 represents an alternative embodiment of a cross section of the housing 30 taking along lines A-A of FIG. 1, depicting a modified cylindrical shape of the reservoir 32 having rounded and parallel sides with no ledges. One advantage of this embodiment is it further enhances laminar flow as the rounded and parallel sides with no ledges results in less potential for the creation of turbulent flow.

The first channel 34 of the housing 30 comprises an opening that allows for fluid to flow from the extension tube 16 to the reservoir 32. The first channel 34 may extend from the outer wall of the housing 30 to the reservoir 32. The first channel 34 may be positioned tangentially from the reservoir 32. Having the first channel 32 positioned tangentially from the reservoir 32 may result in increasing the circumferential flow and minimizing turbulent flow of fluid within the reservoir 32. The first channel 34 may be comprised of multiple diameters varying in size up to 3 mm. The first channel 34 has at least a first diameter 70, a second diameter 72, and a third diameter 74. The third diameter 74 of the first channel 34 is smaller than the second diameter 72. The first channel 34 further comprises a first channel longitudinal axis L1.

The protrusion 38 of the housing 30 is a tapered piece of the housing 30 that is spaced toward the first channel longitudinal axis L1 for a selected distance. The protrusion 38 is comprised of at least two segments, first protrusion segment 94 and second protrusion segment 96. Second protrusion segment 96 may be formed from a gradually tapering section of the first channel 34 wall. First protrusion segment 94 may be formed from a cylindrical section of the reservoir 32 wall. The first protrusion segment 94 and second protrusion segment 96 may have slightly curved wall profiles to enhance the circumferential flow pattern. One advantage of the protrusion 38 is that the at least some of fluid is redirected by the second protrusion segment 96 across the first channel longitudinal axis L1. Such redirection of fluid results in the formation and maintenance of circumferential fluid flow within the reservoir 32. This circumferential fluid flow within the reservoir 32 results in a more laminar fluid flow pattern, higher flow rates, and higher fluid pressure through the infusion set 1.

The second channel 36 comprises an opening that allows for fluid to flow through the reservoir 32. The second channel 36 may be positioned tangentially from the reservoir 32. Having the second channel 36 positioned tangentially from the reservoir 32 may result in increasing the circumferential fluid flow and minimizing turbulent flow of fluid within the reservoir 32. The second channel 36 may be comprised of multiple diameters varying in size up to 1.6 mm. The second channel 36 has at least a first diameter 76, a second diameter 78, and a third diameter 80. The second channel 36 has a second channel longitudinal axis L2. The second channel longitudinal axis L2 may be substantially perpendicular to the first channel longitudinal axis L1. The third diameter 80 of the second channel is larger than the second diameter 78 of the second channel 36. As the second channel 36 tapers, the taper gradually decreasing in size from the third diameter 80 of the second channel 36 to the second diameter 78 of the second channel 36. The advantage of the second channel 36 tapering from the third diameter 80 to the second diameter 78 is that it allows for less turbulent fluid flow through the second channel 36 of the reservoir 32 and the needle lumen 92.

The outer diameter 86 of the needle 2 can be sized up to 2 mm. The inner diameter 88 of the needle 2 can be sized up to 1.2 mm. The second diameter 78 of the second channel 36 may be substantially equal to the inner diameter 88 of the needle. The first diameter 76 of the second channel 36 may be substantially equal to the outer diameter 86 of the needle.

The extension tube 16 of the device comprises an extension tube proximal end 18 and an extension tube distal end 20. The extension tube 16 has an extension tube outer diameter 82 that can be sized up to 3 mm. The extension tube 16 also has an extension tube inner diameter 84 that can be sized up to 2.24 mm. The first diameter 70 of the first channel 34 may be substantially equal to the outer diameter 82 of the extension tube 16. The second diameter 72 of the first channel 34 may be substantially equal to the inner diameter 84 of the extension tube 16.

Figure 7:
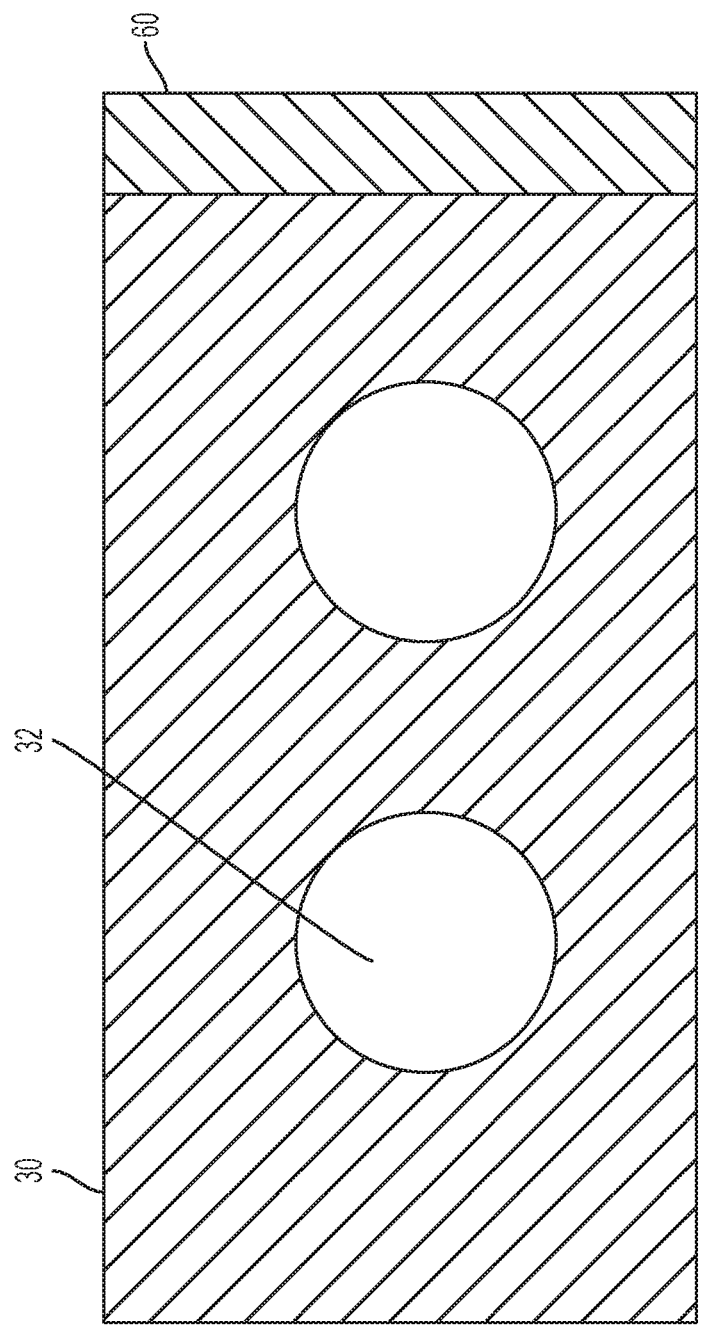
FIG. 7 is a cross section of the housing along the line A-A in FIG. 1 illustrating the reservoir in an alternative embodiment.

Referring now to FIG. 3C, the reservoir 32 of the housing 30 may have a toroidal shape defined as a surface generated by a plane closed curve that is rotated about a line that lies in the same plane as the curve, but does not intersect the curve. The toroidal shape of the reservoir is similar to the reservoir described in U.S. Pat. No. 5,951,512, filed May 28, 1996 and is hereby incorporated by reference. The shape of the reservoir 32 of this invention has many advantages over a prior art infusion needle having a 90-degree bend in the fluid path reservoir. The toroidal shape of the reservoir 32 may ensure that there are no angular junctions between any portions of the reservoir 32. According to the principles of fluid mechanics, the efficiency of fluid flowing in a container is lower near the walls of a container. In addition, the efficiency of fluid flow is lower in any corners of the container where different elements are joined together. The more acute the angle at the point where the elements are joined together, the less efficient the flow is. FIG. 7 represents a cross section of the housing 30 taking along lines A-A of FIG. 1, depicting the toroidal shape of the reservoir 32 with circular walls.

The purpose of the shape of the reservoir 32, such as a cylindrical shape shown in the embodiment of FIG. 3A or a toroidal shape shown in FIB. 3C is to enhance laminar flow of fluid through the first channel 34, extension tube lumen 90, second channel 36, and needle lumen 92. The reservoir shape with tangential first 34 and second 36 channels creates a circumferential fluid flow pattern with laminar fluid characteristics, compared with the turbulent flow fluid characteristics of prior art infusion sets.

Figure 3D:
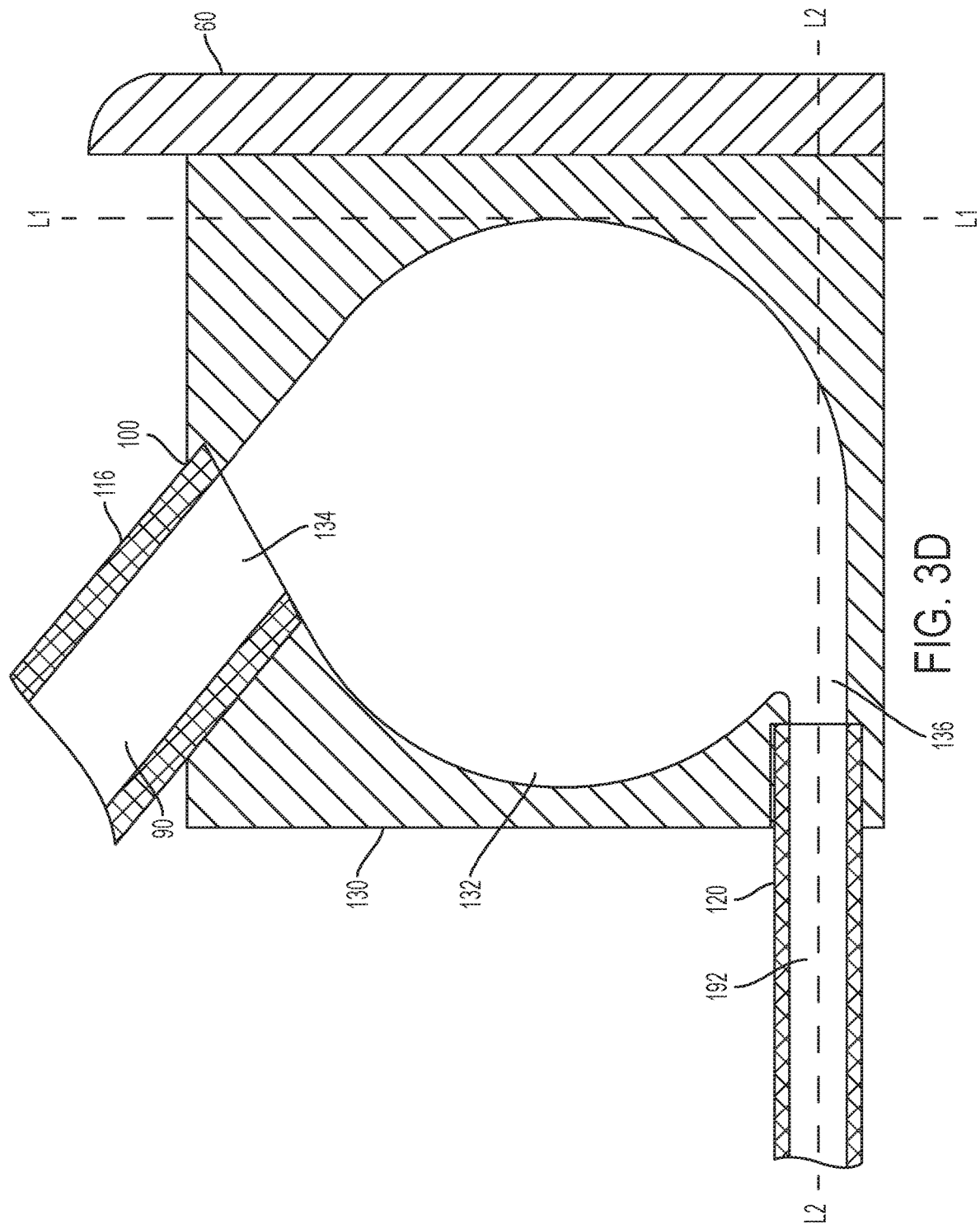
FIG. 3D is a cross section of the housing in another embodiment.

Referring now to FIG. 3D, in yet another embodiment of the infusion device 1 a first channel 134 of a housing 130 may be off-set from a longitudinal axis L1 by up to 45 degrees. The first channel 134 opening in the housing 130 of this embodiment is positioned closer to the midpoint 100 of the housing 130 outer wall compared with the other embodiments. First channel 134 may follow an arced or curved pathway along a tangent to the reservoir 132. Fluid flowing into first channel 134 will begin to form a circumferential flow pattern within the reservoir 132 due to both the curved channel path and the first channel 134 reservoir entry angle along the tangent. Similarly, although not shown in FIG. 3D, second channel 136 may be off-set from longitudinal axis L2 by up to 45 degrees. Second channel 136 opening in housing 130 outer wall may be positioned closer to a midpoint of the housing outer wall compared with the other embodiments. Second channel 136 may also follow an arced or curved pathway along a tangent along the reservoir 132 wall. Fluid being aspirated through the system of this embodiment may begin to form a circumferential flow pattern within the second channel 136 due to the curved channel profile and the second channel 136 reservoir 132 entry angle along the tangent.

Figure 4A:
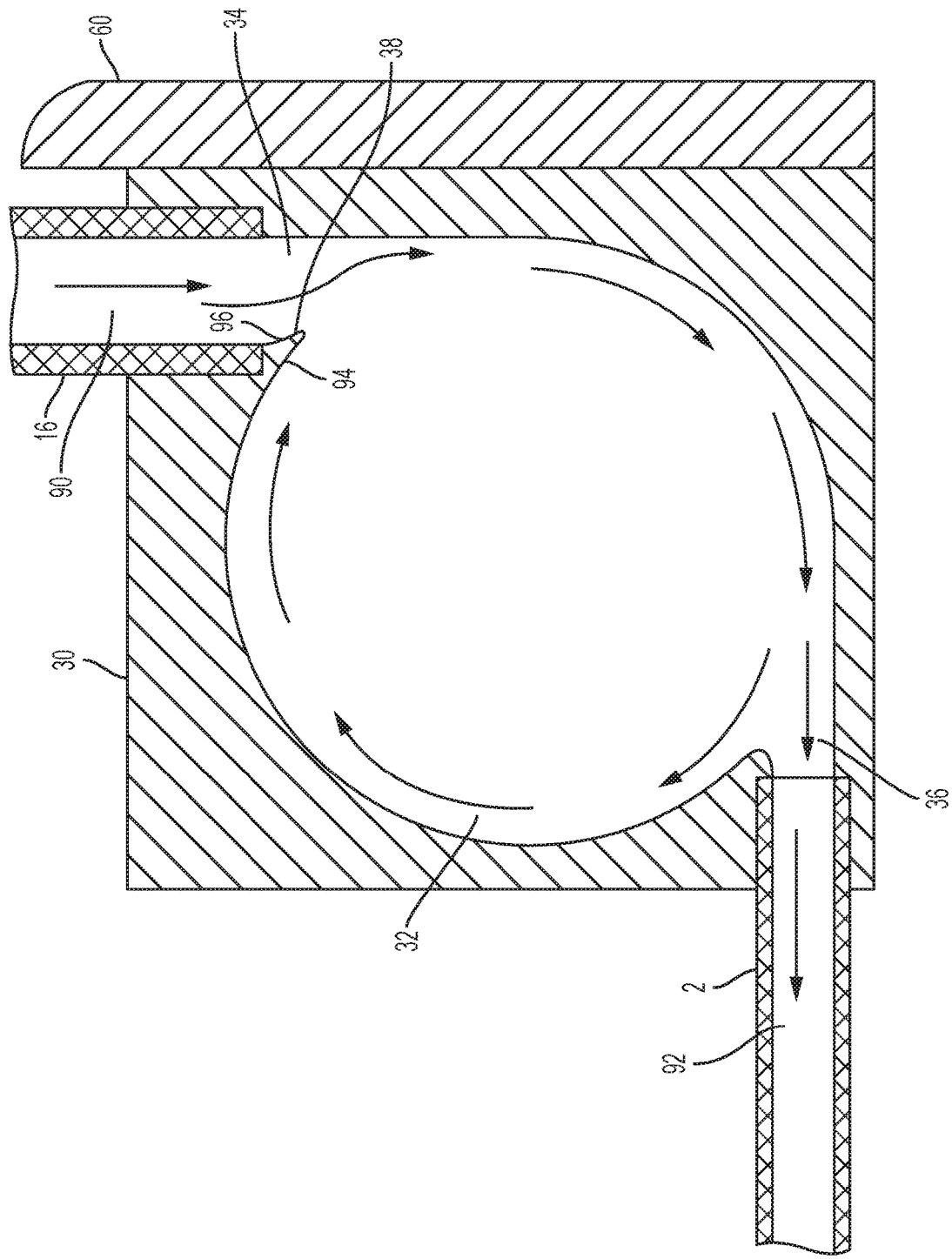
FIG. 4A is a cross section of the housing illustrating the circumferential flow of fluid through the reservoir as a result of an infusion of fluid.

Referring now to FIG. 4A, the arrows represent the direction of fluid flow when infusing fluid through the infusion set 1. Fluid flows from the fluid source, through the infusion tubing 10 and through an extension tube lumen 90. The fluid then flows through the first channel 34 and contacts the second protrusion segment 96, redirecting the fluid across the first channel longitudinal axis L1 and toward the wall of the reservoir 32. The fluid continues to flow in a circumferential direction along the curved wall of the reservoir 32. As the fluid flows along the curved wall of the reservoir 32, a selected amount of fluid will enter the second channel 36 of the reservoir 32 and exit through the needle lumen 92 into an injection site, such as a vascular access port. Any fluid that has not entered into second channel 36 will travel along the reservoir wall away from the second channel longitudinal axis L2 and back toward the first channel 34, continuing the circumferential flow of fluid within the reservoir 32 and creating a flushing effect within the reservoir 32. This flushing effect will result in higher flow rates and fluid pressure rates.

Figure 4B:
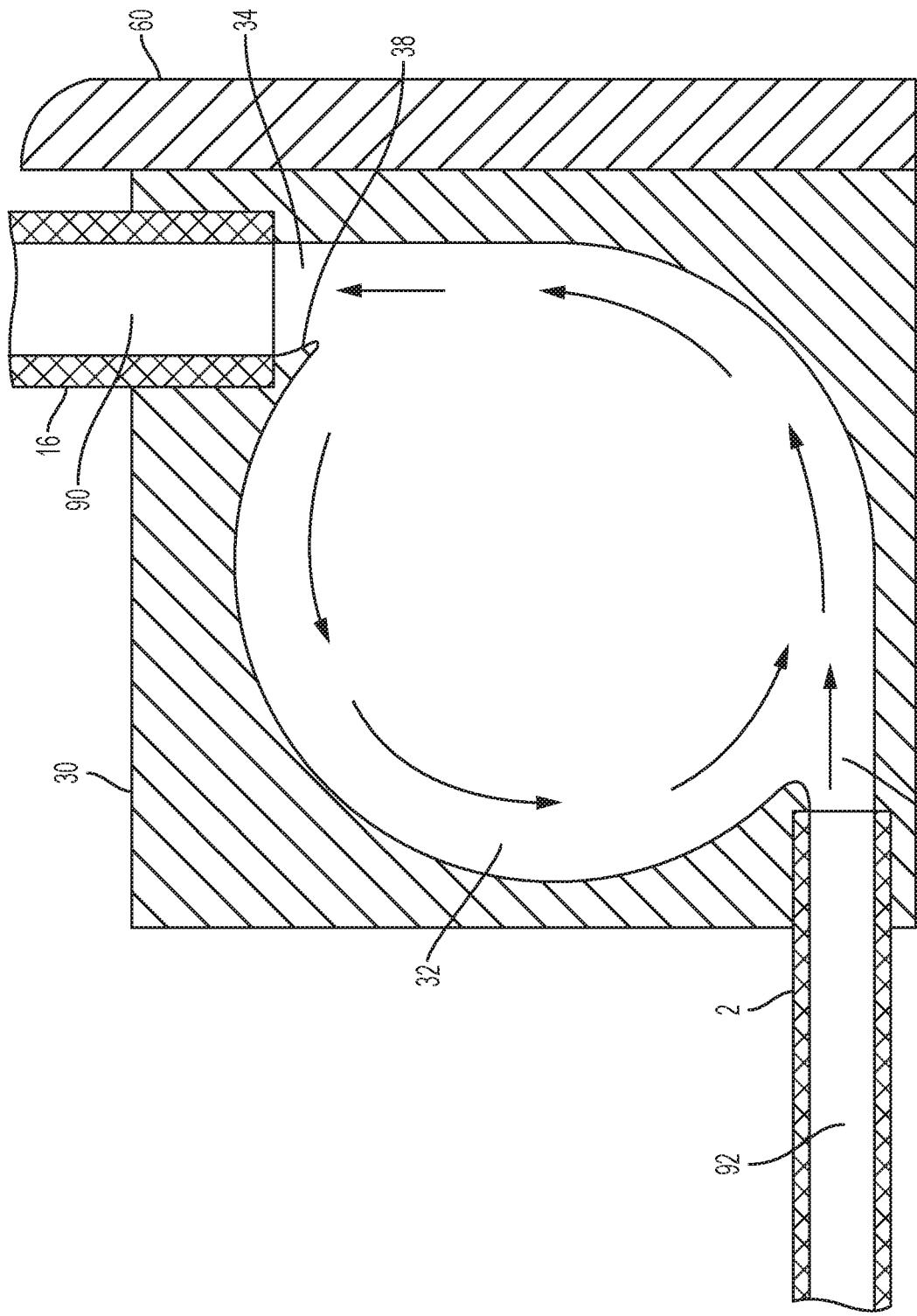
FIG. 4B is a cross section of the housing illustrating the circumferential flow of fluid through the reservoir as a result of an aspiration of fluid.

Referring now to FIG. 4B, the arrows represent the direction of fluid flow when aspirating through the infusion set 1. One example of when fluid may be aspirated through the infusion set 1 is when fluid is flowed from an aspiration site, such as implantable vascular access port, through the infusion set 1 during an apheresis or dialysis procedure. During aspiration, the fluid flows through the needle lumen 92 and into the second channel 36 along the second channel longitudinal axis L2. As the fluid exits the second channel 36 and enters the reservoir 32, the fluid flows along the tangent between the second channel 36 and the wall of the reservoir 32. As the fluid continues to flow along the curved wall of the reservoir 32, a selected amount of fluid will travel into the first channel 34 and through the extension tube lumen 90. Any fluid that has not entered into first channel 34 will travel along the reservoir 32 wall away from the first channel longitudinal axis L1 and back toward the second channel 36, continuing the circumferential flow of fluid within the reservoir 32.

A method for infusing fluid through the infusion set 1 will now be described. First, the infusion tubing distal end 14 is connected to a luer connection at the extension tube proximal end 18, allowing for fluid communication between the infusion tubing 10 and the extension tube 16. After the infusion tubing 10 and the extension tube 16 are connected, the needle 2 may be inserted into the septum of an implanted vascular access port (not shown), allowing for fluid communication between the infusion set 1 and the reservoir of the implanted vascular access port. A user initiates fluid flow through the infusion tubing 10, through the extension tube 16, and into housing 30 through the first channel 34. Next, the fluid flows through the first channel 34 and at least some of the fluid contacts the first protrusion segment 96, thereby redirecting the fluid along the wall of the reservoir 32. This redirection of fluid flow initiates and maintains the circumferential flow within the reservoir 32. The fluid continues to flow along the reservoir wall 32 and enters the second channel 36, entering the lumen 92 of the needle 2 and into the patient. After the infusion has been completed, the user may remove the needle and the infusion set 1 from the patient. The user may grasp the needle holder 60 to aid in the removal of the infusion set 1. This method may include the steps of securing the needle within a safety mechanism as described in U.S. Pat. No. 6,676,633, filed Oct. 24, 2002.

A method for aspirating fluid through the infusion set 1 will now be described. During apheresis procedures, aspiration and infusion of blood will occur simultaneously, so multiple infusion sets would be necessary and connected to an implanted vascular access port with multiple reservoirs. First, the user may insert the needle 2 into the septum of an implanted vascular access port (not shown), allowing for fluid communication between the infusion set 1 and the reservoir of the implanted vascular access port. Next, the user may connect the infusion tubing 10 with a medical device commonly used for apheresis procedures. Upon aspiration by the user, the fluid may exit from the implantable access port and flow into the needle lumen 92. Next, the fluid may flow through the second channel 36 and along the reservoir 32 wall. The fluid continues to flow along the reservoir wall 32 and enters the first channel 34, entering the lumen 90 of the extension tube 16. After the aspiration has been completed, the user may remove the needle and the infusion set 1 from the patient. The user may grasp the needle holder 60 to aid in the removal of the infusion set 1. This method may include the steps of securing the needle within a safety mechanism as described in U.S. Pat. No. 6,676,633, filed Oct. 24, 2002.

The invention claimed is:

1. A device comprising:
   a needle comprising a needle proximal end;
   an extension tube an extension tube distal end; and
   a housing comprising:
   a reservoir having a cylindrical shape;
   a first tangential channel located along a tangent to the reservoir in fluid communication with the extension tube distal end; and
   a second tangential channel located along a tangent to the reservoir in fluid communication with the needle proximal end.

2. The device of claim 1, wherein the housing further comprises a protrusion extending towards a first channel longitudinal axis.

3. The device of claim 2, wherein the protrusion comprises a first protrusion segment and a second protrusion segment.

4. The device of claim 3, wherein the first protrusion segment is formed from a section of a wall of the reservoir and the first protrusion segment comprises a curved profile.

5. The device of claim 3, wherein the second protrusion segment is formed from a section of a wall of the first tangential channel and the second protrusion segment comprises a curved profile.

6. The device of claim 1, wherein the reservoir is configured to provide a fluid with a circumferential flow and laminar flow characteristics.

7. The device of claim 1, wherein the reservoir of the housing is toroidal in shape.

8. The device of claim 1, wherein the reservoir of the housing is spherical in shape.

9. The device of claim 1, wherein the first tangential channel and the second tangential channel follow an arced or curved pathway of the reservoir.

10. The device of claim 1, wherein the first tangential channel and the second tangential channel are in fluid communication with the reservoir along a tangential angle.

11. A method comprising the steps of:
    accessing a site with an infusion set, the infusion set comprising:
        a needle comprising a needle proximal end;
        an extension tube comprising an extension tube distal end; and
        a housing comprising:
            a reservoir having a cylindrical shape;
            a first tangential channel located along a tangent to the reservoir in fluid communication with the extension tube distal end; and
            a second tangential channel located along a tangent to the reservoir in fluid communication with the needle proximal end;
    flowing a fluid through the housing such that the fluid has a circumferential flow pattern with laminar fluid characteristics.

12. The method of claim 11, wherein the first tangential channel and the second tangential channel are in fluid communication with the reservoir along a tangential angle to provide the fluid with a circumferential flow pattern and laminar fluid characteristics.

13. The method of claim 11, wherein the first tangential channel and the second tangential channel follow an arced or curved pathway to provide the fluid with a circumferential flow pattern and laminar fluid characteristics.

14. The method of claim 13, wherein the housing further comprises a protrusion configured to direct the fluid toward a wall of the reservoir in a direction away from a first channel longitudinal axis.

15. The method of claim 13, wherein the step of flowing a fluid through the housing further comprises:
    flowing the fluid across the first tangential channel and the second tangential channel.

16. A method comprising the steps of:
    accessing a site with an infusion set, the infusion set comprising:
        a needle comprising a needle proximal end;
        an extension tube comprising an extension tube distal end; and
        a housing comprising;
            a reservoir having a shape selected from a group comprising either a cylinder or a toroid;
            a first tangential channel to provide a fluid with circumferential flow within the reservoir, wherein the first tangential channel is positioned along a first arced or curved pathway of a first tangential angle relative to the reservoir;
            a second tangential channel to provide the fluid with circumferential flow within the reservoir, wherein the second tangential channel is positioned along a second arced or curved pathway of a second tangential angle relative to the reservoir; and
            a protrusion comprising:
                a first protrusion segment having a curved profile to enhance the circumferential flow of the fluid within the reservoir;
                a second protrusion segment having a curved profile to enhance the circumferential flow of the fluid within the reservoir;
    flowing the fluid through the housing.

17. The method of claim 12, wherein the step of flowing a fluid through the housing may further comprise such that the fluid has laminar fluid characteristics a laminar flow pattern.

18. The method of claim 12, wherein the step of flowing a fluid through the housing further comprises flowing the fluid across the first tangential channel and the second tangential channel to enhance laminar fluid characteristics of the fluid within the reservoir.

* * * * *

UNITED STATES PATENT AND TRADEMARK OFFICE
CERTIFICATE OF CORRECTION

| | | |
|---|---|---|
| PATENT NO. | : 10,912,885 B2 | Page 1 of 1 |
| APPLICATION NO. | : 16/053690 | |
| DATED | : February 9, 2021 | |
| INVENTOR(S) | : Shannon Maguire and Anthony Hien | |

It is certified that error appears in the above-identified patent and that said Letters Patent is hereby corrected as shown below:

In the Claims

Column 8, Line 33, Claim 1 change to:
--an extension tube comprising an extension tube distal end; and--

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*